United States Patent
Kressner et al.

(10) Patent No.: US 7,675,203 B2
(45) Date of Patent: Mar. 9, 2010

(54) ELECTRIC DRIVE UNIT FOR GENERATING AN OSCILLATING DISPLACEMENT

(75) Inventors: Gerhard Kressner, Altenstadt (DE); Alexander Schroter, Steinbach (DE); Christian Junk, Eschborn (DE); Peter Hilfinger, Bad Homburg (DE); Hansjörg Reick, Steinbach (DE); Bernhard Kraus, Braunfels (DE); Uwe Schober, Steinbach (DE)

(73) Assignee: Braun GmbH, Kromberg (DE)

( * ) Notice: Subject to any disclaimer, the term of this patent is extended or adjusted under 35 U.S.C. 154(b) by 350 days.

(21) Appl. No.: 10/577,203

(22) PCT Filed: Oct. 23, 2004

(86) PCT No.: PCT/EP2004/012000

§ 371 (c)(1),
(2), (4) Date: Sep. 24, 2007

(87) PCT Pub. No.: WO2005/043724

PCT Pub. Date: May 12, 2005

(65) Prior Publication Data

US 2008/0185922 A1    Aug. 7, 2008

(30) Foreign Application Priority Data

Oct. 29, 2003    (DE)    ................. 103 50 445

(51) Int. Cl.
*H02K 33/00*    (2006.01)
(52) U.S. Cl. ................. 310/36; 310/68 R; 310/37; 310/38; 310/39
(58) Field of Classification Search ............... 310/36, 310/68 R, 37, 38, 39; *H02K 33/00*
See application file for complete search history.

(56) References Cited

U.S. PATENT DOCUMENTS

| | | | | |
|---|---|---|---|---|
| 3,430,296 | A | * | 3/1969 | Mackie ............... 19/106 A |
| 3,491,258 | A | | 1/1970 | Siefert |
| 4,135,119 | A | * | 1/1979 | Brosens ............... 318/128 |
| 4,146,020 | A | * | 3/1979 | Moret et al. ........... 601/96 |
| 4,187,452 | A | | 2/1980 | Knappe |
| 4,543,718 | A | | 10/1985 | Duescher |
| 5,528,411 | A | | 6/1996 | Burdenko |
| 5,613,259 | A | * | 3/1997 | Craft et al. ........... 15/22.1 |
| 7,554,225 | B2 | * | 6/2009 | Kraus et al. ........... 310/36 |
| 2004/0010871 | A1 | * | 1/2004 | Nishinaka et al. ....... 15/22.2 |
| 2006/0255664 | A1 | * | 11/2006 | Kraus et al. ........... 310/36 |

* cited by examiner

*Primary Examiner*—Quyen Leung
*Assistant Examiner*—John K Kim
(74) *Attorney, Agent, or Firm*—Fish & Richardson P.C.

(57) ABSTRACT

An electric drive unit for generating an oscillating movement, having a stator, a rotor, a torsion element and a tuning element. The tuning element acts upon the torsion element and serves to mechanically tune the resonant frequency of the drive unit.

14 Claims, 5 Drawing Sheets

B - B

C - C

C - C

ELECTRIC DRIVE UNIT FOR GENERATING AN OSCILLATING DISPLACEMENT

TECHNICAL FIELD

This application relates to an electric drive unit for generating an oscillating movement.

BACKGROUND

Drive units for generating an oscillating movement are used, for example, in electric toothbrushes or electric razors. For example, Pat. No. DE 28 20 437 A1 discloses an electric toothbrush with an oscillating armature motor. The oscillating armature motor is used for realizing an oscillating rotational movement of a shaft that carries a brush element. The rotational movements are influenced by torsion springs and damping elements such that a desired motion sequence is adjusted.

U.S. Pat. No. 5,613,259 discloses an oscillating appliance in the form of an electric toothbrush. This appliance features a mechanical oscillator that is driven by an electric motor. The electric motor is controlled in dependence on the oscillating frequency of the mechanical oscillator that is determined by means of a sensor, such that the mechanical oscillator remains resonant under a varying load. The mechanical oscillator is realized in the form of a spring-mass system that may comprise a coil spring or a torsion rod. In order to achieve a substantially optimal operation of the electric drive unit for generating an oscillating movement, the drive unit should be excited with a frequency that substantially corresponds or lies close to its resonant frequency. However, the resonant frequency not only changes with the load of the drive unit, but is also detuned due to manufacturing tolerances associated with series production. Although regulating the excitation frequency can compensate for this detuning, such control results in increased manufacturing costs. Moreover, changing the excitation frequency is undesirable in certain applications.

SUMMARY

In one aspect, an electric drive unit for generating an oscillating movement has a stator, a rotor and a torsion element. Moreover, a tuning element is provided that acts upon the torsion element, serving to mechanically tune the resonant frequency of the drive unit.

Certain implementations have the advantage that the drive unit allows for an optimal conversion of the electric driving energy into the oscillating movement regardless of possible manufacturing tolerances, such that a comparatively low electrical power suffices for the operation of the drive unit.

The drive unit is preferably realized such that the tuning element fixes the torsion element at a variable location of the torsion element. The tuning element may be arranged on the stator, such that it can be displaced and fixed in position. The tuning element may be displaceable parallel to the longitudinal axis of the drive unit. For this purpose, the tuning element may engage, for example, into at least one groove in the stator. A design of this type can be realized with a relatively low expenditure, and makes it possible to easily tune the resonant frequency of the drive unit.

With respect to its simple handling, it can be particularly advantageous to provide the tuning element in the form of a clamping device. In this case, the tuning element may have, for example, two parts and at least one connecting element for pulling together the two parts.

The torsion element can be fixed on the rotor. In one preferred implementation of the drive unit, the rotor features a hollow shaft. In this case, it can be particularly advantageous to arrange the torsion element at least partially within the hollow shaft, making it possible to provide the drive unit in a very compact fashion. The torsion element can be provided in the form of a torsion rod that can be manufactured with very strict tolerances and hardly requires any structural space, particularly when implemented in combination with the hollow shaft.

The drive unit may feature a housing with a recess in the region of the tuning element. This makes it possible to carry out the tuning of the resonant frequency when the drive unit is already completely assembled.

In one preferred embodiment of the drive unit, the stator features permanent magnets and at least one coil. The rotor preferably features an armature of a magnetizable material.

Another aspect of the invention features a small electric appliance equipped with the above-described drive unit. The small appliance can be realized in the form of an electric toothbrush or an electric razor. Appliances of this type are frequently operated independently of the electric power supply by means of a battery. The comparatively low power consumption of the drive unit has positive effects on the time of operation that can be achieved with one battery charge.

Another aspect of the invention features a method of manufacturing an electric drive unit for generating an oscillating movement. The drive unit features a stator, a rotor and a torsion element. The resonant frequency of the drive unit is mechanically tuned by the torsion element after the assembly of the drive unit.

The scope of the method includes embodiments in which a region of the torsion element that participates in the oscillating movement can be varied in order to adjust the drive unit to a desired resonant frequency. For this purpose, the torsion element can be fixed on a tuning element. The location where the tuning element engages on the torsion element can be chosen such that the drive unit has the desired resonant frequency. In order to achieve a reliable tuning of the resonant frequency, the drive unit can be excited, such that it carries out an oscillating movement, and the location of the torsion element where the tuning element needs to be fixed can be determined from the oscillating movement of the drive unit. In one preferred embodiment of the method, an excitation by pulses is employed to cause the oscillation of the drive unit. The location of the torsion element where the tuning element needs to be fixed can be determined, for example, from the decay behavior of the oscillating movement. The torsion element is preferably fixed in the rotational position that the rotor assumes when the drive unit is switched off.

Other aspects, features, and advantages will be apparent from the following detailed description, the drawings, and the claims.

DETAILED DESCRIPTION

Figure 1:
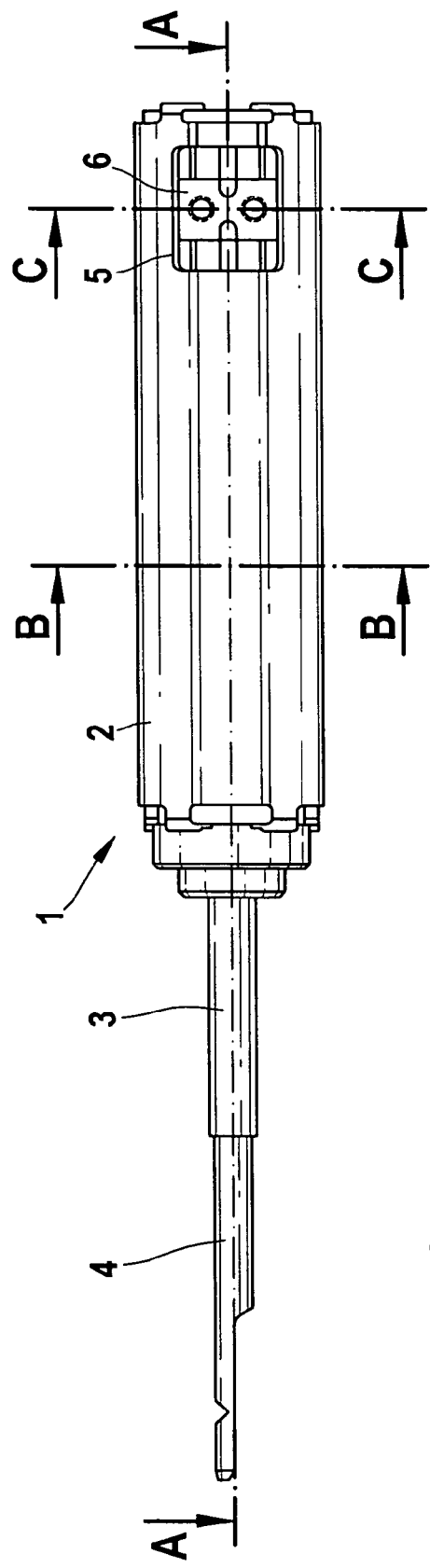
FIG. 1 is a top view of a first embodiment of a drive unit.

Referring to FIG. 1, drive unit 1 features an elongated housing 2, from one face of which a hollow shaft 3 protrudes, extending parallel to the longitudinal axis of the drive unit 1. A connection piece 4 for receiving a not-shown toothbrush attachment is coaxially inserted into the axial end of the hollow shaft 3 that is situated outside the housing 2, and then connected to the hollow shaft 3 in a rotationally rigid fashion. The housing 2 features a window-shaped recess 5 on one of its longitudinal sides, for example in the end region opposite to the face on which the hollow shaft 3 protrudes from the housing 2. An adjusting element 6 arranged in the interior of the housing 2 is visible through the recess 5, wherein this adjusting element can be displaced parallel to the longitudinal axis of the drive unit 1, and is described in greater detail below. Details regarding the internal design of the drive unit 1 are illustrated in the sectional representations according to FIGS. 2-5, and in the sectional representation of a second embodiment according to FIG. 6.

Figure 2:
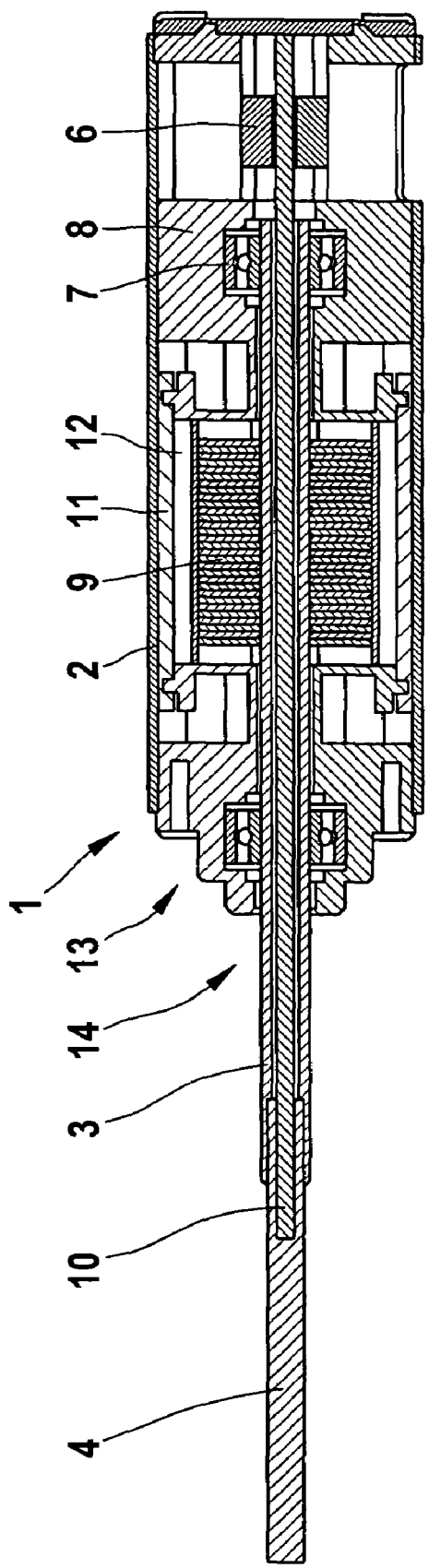
FIG. 2 is a longitudinal section through the first embodiment of the drive unit along the line A-A in FIG. 1.
Figure 3:
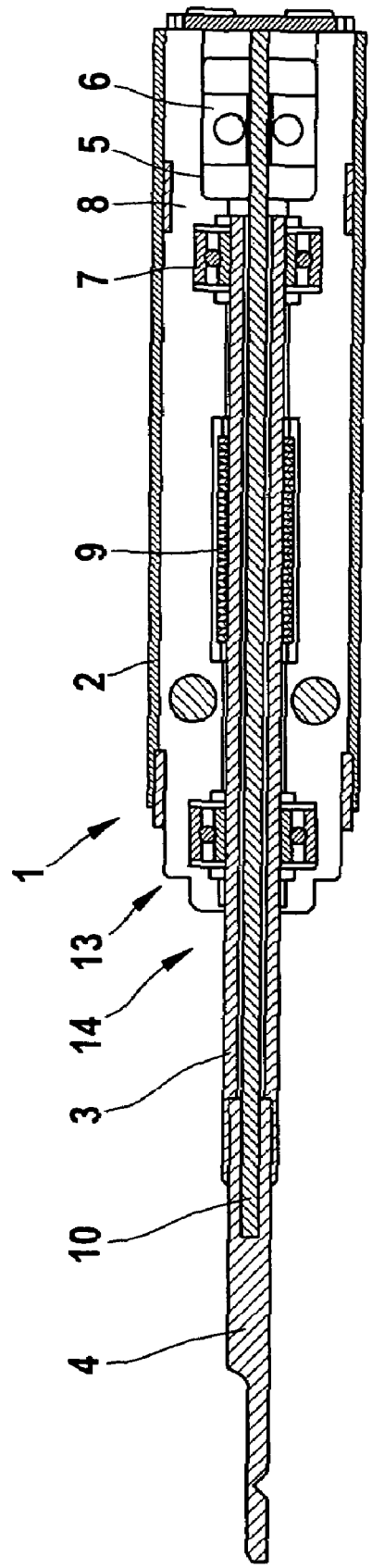
FIG. 3 is another longitudinal section through the first embodiment of the drive unit, wherein the plane of section is turned relative to FIG. 2 by 90° about the longitudinal axis of the drive unit.

Referring to FIGS. 2 and 3, the hollow shaft 3 continues into the housing 2 and is rotatably supported relative to the housing 2 in two bearings 7. The bearings 7 are arranged in a coil form 8. An armature 9 is arranged on the hollow shaft 3 in a rotationally rigid fashion between the two bearings 7. A torsion rod 10 extends within the hollow shaft 3 coaxial to the hollow shaft 3 and protrudes from the hollow shaft 3 with both of its axial ends. In the region of its first axial end, the torsion rod 10 is connected to the connection piece 4, and therefore also to the hollow shaft 3 in a rotationally rigid fashion. In the vicinity of its second axial end, the torsion rod 10 is clamped into the adjusting element 6 in a rotationally rigid fashion, and thus connected to the housing 2 in a rotationally rigid fashion. This means that a torsionally elastic suspension of the hollow shaft 3 including the connection piece 4 and the armature 9 can be realized on the housing 2 by means of the torsion rod 10.

Permanent magnets 12 are arranged radially adjacent to the armature 9 on carrier plates 11. The carrier plates 11 are arranged on the inside of the housing 2 diametrically opposite of one another. A stationary stator 13 and a rotor 14 that is rotatable relative to the stator 13 are realized with the components illustrated in FIGS. 3 and 4. The housing 2, the coil form 8, the carrier plate 11 and the permanent magnets 12 can be assigned to the stator 13. The hollow shaft 3 with the connection piece 4 and the armature 9 form the components of the rotor 14. The stator 13 and the rotor 14 are coupled to one another in a torsionally elastic fashion with the aid of the torsion rod 10.

Figure 4:
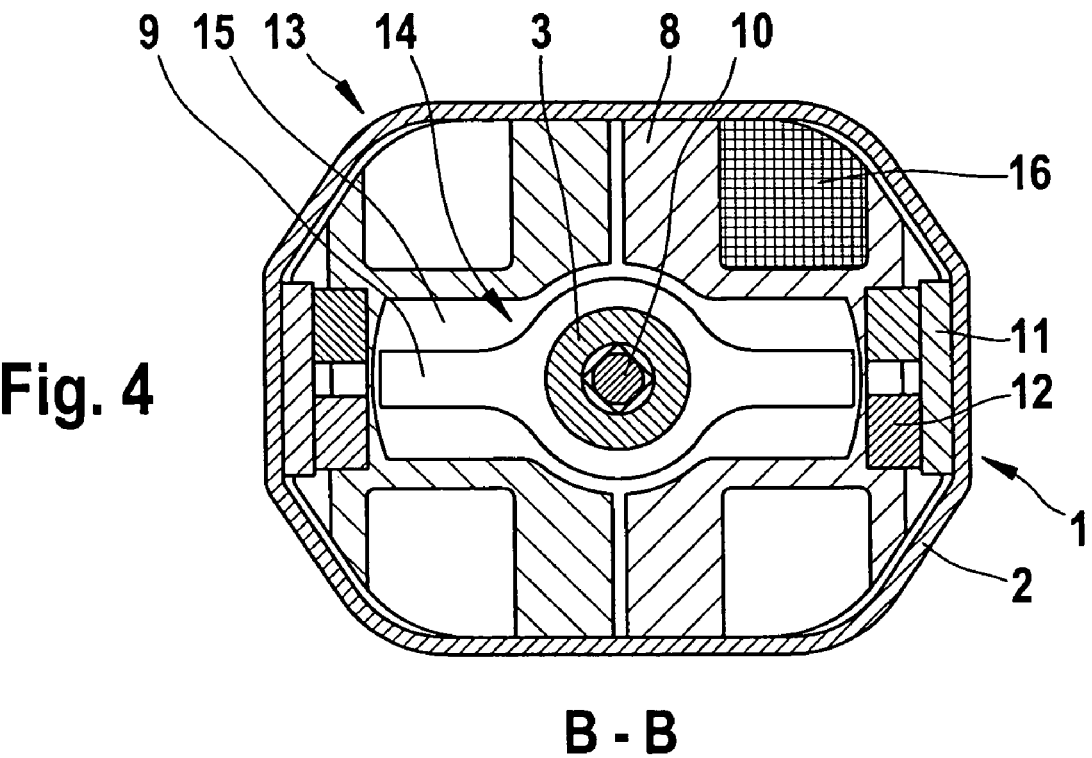
FIG. 4 is a cross section through the first embodiment of the drive unit along the line B-B in FIG. 1.

Referring to FIG. 4, the armature 9 has an elongated cross-sectional shape and is arranged in an oblong hollow space 15 in such a way that it can be slightly turned in both rotating directions relative to the idle position shown. In this implementation, the coil form 8 carries at least one coil 16 that is only partially illustrated in FIG. 4. When a current flows through the coil 16, a magnetic field is generated in the armature 9, such that a magnetic interaction with the permanent magnets 12 occurs in the region of the radial surfaces of the armature 9 that are situated adjacent to the permanent magnets 12. This magnetic interaction causes the armature 9 to be displaced from its idle position, and therefore the hollow shaft 3 to be slightly turned. An alternating current feed to the coil 16 makes it possible to achieve an alternating movement of the armature 9 in both rotating directions referred to its idle position, such that an oscillating rotational movement of the rotor 14 occurs. This oscillating rotational movement is promoted by the torsion rod 10 that respectively turns the rotor 14 back into the idle position of the armature 9 and forms an oscillatory spring-mass system together with the rotor 14.

The amplitude of the oscillating rotational movement becomes particularly high if the excitation, by means of the current-carrying coil 16, takes place at the resonant frequency of the spring-mass system. The excitation energy can be transmitted most effectively within the range of the resonant frequency, such that the excitation energy required for a desired amplitude assumes a minimum value. In order to operate the drive unit 1 as efficiently as possible, the resonant frequency of the spring-mass system should correspond as precisely as possible to the excitation frequency, or to a predetermined value in the vicinity of the excitation frequency. However, in the series production of several drive units 1, the resonant frequencies are detuned due to manufacturing-related tolerances of the components forming drive unit 1. In a preferred implementation, the resonant frequency of the spring-mass system can be mechanically tuned after its assembly. The tuning can be achieved by varying the effective length of the torsion rod with the aid of the adjusting element 6. This procedure is discussed in detail below with reference to FIG. 5.

Figure 5:
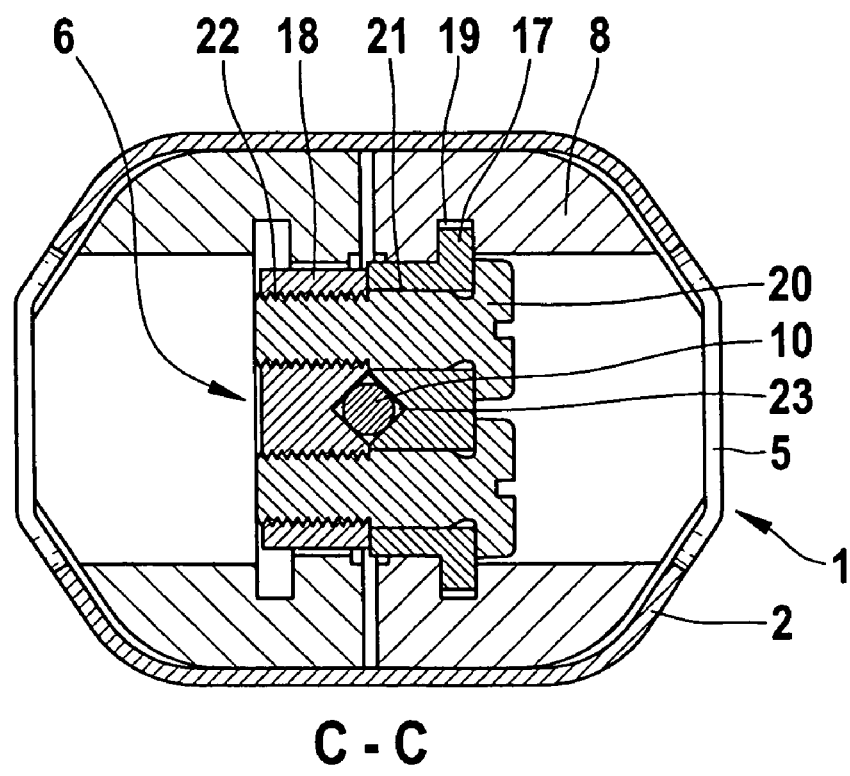
FIG. 5 is a cross section through the first embodiment of the drive unit along the line C-C in FIG. 1.

FIG. 5 shows a cross section through the first embodiment of the drive unit 1 along the line C-C in FIG. 1. Consequently, the plane of section extends through the adjusting element 6 that consists of an upper part 17 and a lower part 18. The parting plane between the upper part 17 and the lower part 18 of the adjusting element 6 extends parallel to the longitudinal axis of the drive unit 1. The upper part 17 of the adjusting element 6 engages into one respective groove 19 in the coil form 8 that extends parallel to the longitudinal axis of the drive unit 1 on both sides, and can be moved in this direction only.

The upper part 17 is screwed to the lower part 18 with two screws 20 that are inserted into through-bores 21 in the upper part 17 of the adjusting element 6 and engage threaded bores in the lower part 18 of the adjusting element 6. When the screws are tightened, the torsion rod 10 is clamped between two splines 23 that are realized parallel to the longitudinal axis of the drive unit 1 in the upper part 17, and in the lower part 18 of the adjusting element 6. The wall surfaces of the splines are pressed against the cylindrical outer surface of the torsion rod 10. This causes the torsion rod 10 to be non-positively fixed on the adjusting element 6. The adjusting element 6 is simultaneously blocked from moving parallel to the longitudinal axis of the drive unit 1 because the torsion rod 10 is rigid in this direction. The screws 20 are accessible through the recess 5 in the housing 2 in order to be tightened and loosened. The tuning of the resonant frequency of the spring-mass system of the drive unit 1 can be carried out as described below. The torsion rod 10 is clamped into the adjusting element 6 in the rotational position that it assumes as its idle position due to the effect of the permanent magnets 12 on the armature 9. Before the torsion rod 10 is fixed in position by tightening the screws 20, a preliminary tuning process can be carried out by displacing the adjusting element 6 into the position in which the desired resonant frequency of the spring-mass system is presumably reached. In this case, the effective length of the torsion rod 10 is adjusted with the aid of the adjusting element 6, such that the resonant frequency of the spring-mass system is influenced accordingly. The effective length of the torsion rod 10 corresponds to the distance between the location at which the torsion rod 10 is fixed on the connection piece 4 and the location at which the torsion rod 10 is fixed on the adjusting element 6. The resonant frequency rises when the effective length of the torsion rod 10 is shortened, i.e., if the adjusting element 6 is displaced toward the hollow shaft 3. Vice versa, the resonant frequency is lowered if the effective length of the torsion rod 10 is extended by increasing the distance between the adjusting element 6 and the hollow shaft 3.

After this preliminary adjustment, the drive unit is excited by pulses such that it carries out an oscillating movement, and the effective resonant frequency of the spring-mass system for the current position of the adjusting element 6 is determined from the decay behavior of the oscillating movement. The deviation between the effective resonant frequency and the desired resonant frequency is then used for determining the distance, by which the adjusting element 6 needs to be displaced in order to reach the desired resonant frequency, for example, with the aid of an empirically prepared table. The adjusting element 6 is then displaced by the determined distance. The position of the adjusting element 6 can be checked with another excitation by pulses. If so required, the adjusting element 6 is readjusted until the effective resonant frequency of the spring-mass system corresponds to the desired resonant frequency with a predetermined accuracy. The adjusting element 6 is then permanently fixed in position.

According to FIGS. 4 and 5, the torsion rod 10 according to the first embodiment of the drive unit 1 has a circular cross section. The scope of the invention also includes alternative designs of the torsion rod 10. Other implementations are possible, for example a second embodiment is illustrated in FIG. 6.

Figure 6:
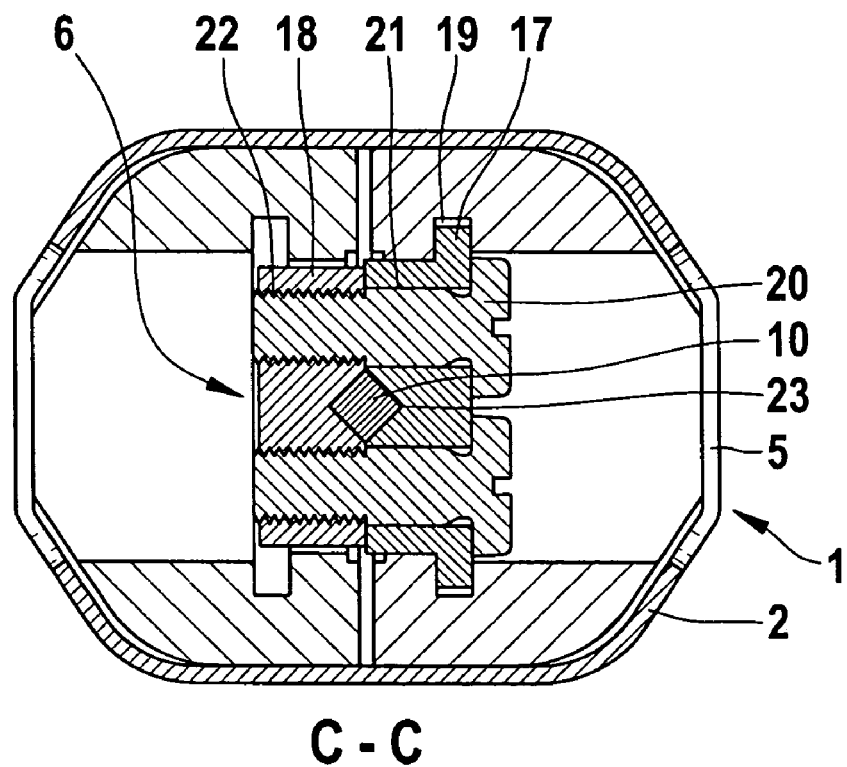
FIG. 6 is a cross section through a second embodiment of the drive unit along the line C-C in FIG. 1.

Referring to FIG. 6, the torsion rod 10 has a square cross section in the second embodiment. The departure from the rotationally symmetrical design of the torsion rod 10 in the second embodiment makes it possible to positively secure the torsion rod 10 with the adjusting element 6 from turning. The splines 23 used in the first embodiment for fixing the torsion rod in the upper part 17 and the lower part 18 of the adjusting element 6 may also be used in this case. The second embodiment of the drive unit 1 also corresponds to the first embodiment with respect to its remaining design and its function.

Other implementations are within the scope of the following claims.

The invention claimed is:

1. An electric drive unit for generating an oscillating movement, the drive unit comprising:
    a stator;
    a rotor comprising a hollow shaft;
    a torsion element comprising a torsion rod at least partially arranged within the hollow shaft and coupling the stator and rotor to one another in a torsionally elastic fashion; and
    a tuning element, which acts upon the torsion element and is configured to be fixed to the torsion rod at selectable positions along the torsion rod to mechanically tune the resonant frequency of the drive unit.

2. The drive unit according claim 1, wherein the tuning element is configured to be displaced with respect to the stator and then fixed in displaced position.

3. The drive unit according to claim 2, wherein the tuning element is displaceable parallel to the longitudinal axis of the drive unit.

4. The drive unit according to claim 2, wherein the tuning element engages into at least one groove in the stator.

5. The drive unit according to claim 1, wherein the tuning element comprises a clamping device.

6. The drive unit according to claim 5, wherein the tuning element comprises two parts and at least one connecting element configured to draw the two parts together.

7. The drive unit according to claim 1, wherein the torsion element is fixed to the rotor.

8. The drive unit according to claim 1, further comprising a housing having a recess arranged to accommodate the tuning element.

9. The drive unit according to claim 1, wherein the stator comprises permanent magnets and at least one coil.

10. The drive unit according to claim 1, wherein the rotor comprises an armature of a magnetizable material.

11. A method of manufacturing an electric drive unit for generating an oscillating movement, wherein the drive unit comprises a stator, a rotor comprising a hollow shaft, a torsion element comprising a torsion rod at least partially arranged within the hollow shaft and coupling the stator and rotor to one another in a torsionally elastic fashion, and a tuning element that acts upon the torsion element and is configured to be fixed to the torsion rod at selectable positions along the torsion rod to mechanically tuning tune the resonant frequency of the drive unit, the method comprising:
    exciting the drive unit to generate an oscillating movement; and
    determining from the oscillating movement a desired location on the torsion element for securing the tuning element to tune a resonant frequency of the drive unit.

12. The method of claim 11, further comprising fixing the torsion element on the tuning element in the desired location.

13. The method according to claim 12, wherein exciting the drive unit comprises exciting the drive unit by pulses.

14. The method according to claim 11, further comprising switching the drive unit off, and then fixing the torsion element in a rotational position that the rotor assumes when the drive unit is switched off.

* * * * *